US010952668B2

(12) United States Patent
Ruwe et al.

(10) Patent No.: US 10,952,668 B2
(45) Date of Patent: Mar. 23, 2021

(54) PILOT WORKLOAD MONITORING SYSTEM

(71) Applicant: Bose Corporation, Framingham, MA (US)

(72) Inventors: Matthew Neil Ruwe, Hopedale, MA (US); Michael Camille Salame, Waltham, MA (US)

(73) Assignee: BOSE CORPORATION, Framingham, MA (US)

(*) Notice: Subject to any disclaimer, the term of this patent is extended or adjusted under 35 U.S.C. 154(b) by 0 days.

(21) Appl. No.: 16/275,522

(22) Filed: Feb. 14, 2019

(65) Prior Publication Data
US 2020/0261017 A1 Aug. 20, 2020

(51) Int. Cl.
G08B 21/00 (2006.01)
A61B 5/00 (2006.01)
A61B 5/0205 (2006.01)
A61B 5/0402 (2006.01)
A61B 5/0476 (2006.01)
(Continued)

(52) U.S. Cl.
CPC ............ A61B 5/486 (2013.01); A61B 5/0205 (2013.01); A61B 5/0402 (2013.01); A61B 5/0476 (2013.01); A61B 5/14551 (2013.01); A61B 5/163 (2017.08); A61B 5/18 (2013.01); A61B 5/6803 (2013.01); B64F 5/60 (2017.01); A61B 5/02405 (2013.01); A61B 5/0531 (2013.01); A61B 5/0816 (2013.01)

(58) Field of Classification Search
CPC ....... A61B 5/486; A61B 5/163; A61B 5/0205; A61B 5/0402; A61B 5/0476; A61B 5/14551; A61B 5/18; A61B 5/6803; A61B 5/02405; A61B 5/0531; A61B 5/0816; B64F 5/60

USPC .......................................................... 340/945
See application file for complete search history.

(56) References Cited

U.S. PATENT DOCUMENTS

2004/0239550 A1* 12/2004 Daly, Jr. ............... G01S 13/723
                                                          342/26 B
2007/0288129 A1* 12/2007 Komer ................. G08G 5/0013
                                                            701/3
(Continued)

FOREIGN PATENT DOCUMENTS

EP          3415416 A1    12/2018

OTHER PUBLICATIONS

PCT International Search Report and Written Opinion for International Application No. PCT/US2020/018096, dated Jun. 30, 2020, 10 pages.
(Continued)

Primary Examiner — Zhen Y Wu
(74) Attorney, Agent, or Firm — Hoffman Warnick LLC

(57) ABSTRACT

Various implementations include approaches for monitoring the workload of a pilot, such as an aircraft pilot. Certain approaches include: receiving flight condition data and aircraft configuration data about an aircraft; comparing the flight condition data and aircraft configuration data with corresponding thresholds to determine flight condition and aircraft configuration workload components; applying respective weights to the flight condition and aircraft configuration workload components; and providing a report indicating a workload for the pilot based upon the weighted flight condition and aircraft configuration workload components.

20 Claims, 6 Drawing Sheets

(51) Int. Cl.
  *A61B 5/1455* (2006.01)
  *A61B 5/18* (2006.01)
  *B64F 5/60* (2017.01)
  *A61B 5/16* (2006.01)
  *A61B 5/08* (2006.01)
  *A61B 5/024* (2006.01)
  *A61B 5/0531* (2021.01)

(56) References Cited

U.S. PATENT DOCUMENTS

| | | | |
|---|---|---|---|
| 2010/0030400 A1* | 2/2010 | Komer | G10L 15/26 |
| | | | 701/3 |
| 2010/0174424 A1 | 7/2010 | Cornell et al. | |
| 2012/0075119 A1* | 3/2012 | Dorneich | G06Q 10/06 |
| | | | 340/945 |
| 2012/0075122 A1* | 3/2012 | Whitlow | B64D 45/0015 |
| | | | 340/963 |
| 2012/0075123 A1* | 3/2012 | Keinrath | G06Q 10/06 |
| | | | 340/963 |
| 2012/0078445 A1 | 3/2012 | Krupansky et al. | |
| 2012/0081236 A1* | 4/2012 | Best | G08G 5/0021 |
| | | | 340/945 |
| 2013/0268146 A1 | 10/2013 | Baudry | |
| 2015/0123820 A1* | 5/2015 | Merle | B64D 45/00 |
| | | | 340/945 |
| 2015/0251771 A1* | 9/2015 | Whitlow | B64D 45/00 |
| | | | 701/3 |
| 2016/0332567 A1* | 11/2016 | Wilson | G01S 19/13 |
| 2017/0324437 A1* | 11/2017 | Ruttler | A61B 5/02438 |
| 2017/0336789 A1* | 11/2017 | Sane | B64C 13/0421 |
| 2018/0054508 A1 | 2/2018 | Yamkovoy et al. | |
| 2018/0251230 A1* | 9/2018 | Chavez | B64D 11/0689 |
| 2018/0304993 A1 | 10/2018 | Offredi et al. | |
| 2018/0364707 A1* | 12/2018 | Bosworth | A61B 5/6801 |
| 2019/0027051 A1* | 1/2019 | Veronesi | G08G 5/06 |
| 2019/0090800 A1* | 3/2019 | Bosworth | B64C 13/02 |
| 2019/0250408 A1* | 8/2019 | Lafon | B64D 43/00 |
| 2019/0318741 A1* | 10/2019 | Songa | G06F 3/167 |
| 2019/0371183 A1* | 12/2019 | Mecklem | G08G 5/0086 |
| 2020/0031495 A1* | 1/2020 | Venkataramana | B64D 47/02 |
| 2020/0070966 A1* | 3/2020 | Alfred | G05D 1/0858 |

OTHER PUBLICATIONS

Mulgund et al., "Situation Awareness Modeling and Pilot State Estimation for Tactical Cockpit Interfaces," Charles River Analytics, dated Aug. 1, 1997, 4 pages.

\* cited by examiner

|  | FC(i) | FC(ii) | AC(i) | AC(ii) | PC(i) | PC(ii) |
|---|---|---|---|---|---|---|
| WCV | 4 | 1 | 7 | -3 | 0 | -2 |
| Control Value | 0.0 | 0.1 | 0.7 | 0.8 | 0.7 | 0.2 |
| Weight | X | X/2 | 3X | X/3 | X/2 | X/5 |
| Weighted WCV | 4X | X/2 | 21X | -1X | 0 | -2X/5 |

PILOT WORKLOAD MONITORING SYSTEM

TECHNICAL FIELD

This disclosure generally relates to aviation systems. More particularly, the disclosure relates to approaches for monitoring pilot workload using data gathered from an aviation headset.

BACKGROUND

Pilot workload monitoring and management is a significant consideration within the aviation industry. However, conventional approaches for monitoring and managing pilot workload focus on physiological data about the pilot, providing an incomplete picture of the pilot's workload.

SUMMARY

All examples and features mentioned below can be combined in any technically possible way.

Various implementations include approaches for monitoring the workload of a pilot, such as an aircraft pilot. Certain approaches include: receiving flight condition data and aircraft configuration data about an aircraft; comparing the flight condition data and aircraft configuration data with corresponding thresholds to determine flight condition and aircraft configuration workload components; applying respective weights to the flight condition and aircraft configuration workload components; and providing a report indicating a workload for the pilot based upon the weighted flight condition and aircraft configuration workload components.

In some particular aspects, a pilot monitoring system includes: a headset; one or more physiological sensors for detecting physiological conditions of an aircraft pilot; and a smart device in communication with the headset and a flight management system, where the smart device includes program code configured to: receive flight condition data and aircraft configuration data about the aircraft from the flight management system; compare the flight condition data with a flight condition threshold to determine a flight condition workload component; compare the aircraft configuration data with an aircraft configuration threshold to determine an aircraft configuration workload component; apply a first weight to the flight condition workload component and a second weight to the aircraft configuration workload component; and output a report indicating a workload for the aircraft pilot based upon the weighted flight condition workload component and the weighted aircraft configuration workload component.

In other particular aspects, a computer-implemented method of monitoring workload for an aircraft pilot during flight of an aircraft includes: receiving flight condition data and aircraft configuration data about the aircraft from a flight management system on the aircraft; comparing the flight condition data with a flight condition threshold to determine a flight condition workload component; comparing the aircraft configuration data with an aircraft configuration threshold to determine an aircraft configuration workload component; applying a first weight to the flight condition workload component and a second weight to the aircraft configuration workload component; and outputting a report indicating a workload for the aircraft pilot based upon the weighted flight condition workload component and the weighted aircraft configuration workload component.

Implementations may include one of the following features, or any combination thereof.

In certain cases, the program code is further configured to: receive physiological condition data about the aircraft pilot from the one or more physiological sensors; compare the physiological condition data with a physiological condition threshold to determine a physiological condition workload component; and apply a third weight to the physiological condition workload component, where the report indicating the pilot workload is further based upon the weighted physiological condition workload component.

In particular aspects, the smart device includes an electronic flight bag, and the report includes at least one of: an in-flight indicator of the workload for the aircraft pilot during a flight, a predictive indicator of the workload for the aircraft pilot at a future time, or a post-flight report of the workload for the aircraft pilot throughout the flight.

In some implementations, the report includes suggested adjustments to at least one aircraft configuration metric to reduce the workload for the aircraft pilot.

In certain cases, at least one of the flight condition threshold or the aircraft configuration threshold is based upon predefined settings specific to the aircraft pilot or a data model defining a physiological fatigue threshold specific to the aircraft pilot.

In particular aspects, a ratio of the first weight to the second weight is variable based upon at least one of: a level of control the aircraft pilot can exert over the aircraft condition, a value of the flight condition workload component or a value of the aircraft configuration workload component.

In certain implementations, the flight condition data and the aircraft configuration data each include data inputs from a plurality of data metrics, the flight condition threshold and the aircraft configuration threshold each includes a plurality of thresholds corresponding with each of the plurality of data metrics, and the first weight and the second weight each include sub-weights applied to each of the respective plurality of data metrics.

In particular aspects, the workload for the aircraft pilot is based upon a data model defining a physiological fatigue threshold for the aircraft pilot, where the data model includes: correlations between flight condition data and physiological fatigue for the aircraft pilot for the plurality of data metrics; and correlations between aircraft configuration data and physiological fatigue for the aircraft pilot for the plurality of data metrics, where at least one of the first weight or the second weight is adjusted based upon a number of the data metrics that deviate from the corresponding thresholds.

In some cases, the flight condition data includes data about at least one of: a weather condition proximate an aircraft flown by the pilot during flight, an altitude of the aircraft during flight, a wind condition proximate the aircraft during flight, a deviation of the aircraft from a planned route, an amount of turbulence experienced by the aircraft during flight, a total flight time for the aircraft, a distance traveled by the aircraft during flight, or an ambient lighting condition proximate the aircraft during flight.

In certain aspects, the physiological sensors are configured to detect physiological condition data including at least one of: a heart rate of the aircraft pilot, a heart rate variability of the aircraft pilot, a blood oxygen saturation level of the aircraft pilot, an electrical activity from the brain of the aircraft pilot, an electrical activity from the heart of the aircraft pilot, a respiration rate of the aircraft pilot, electrodermal activity of the aircraft pilot, or eye movement of the aircraft pilot.

In particular implementations, the aircraft configuration data includes data about at least one of: power settings of the aircraft, a position of landing gear on the aircraft, a position of wing flaps on the aircraft, a weight of the aircraft, a balance of the aircraft, a number of crew members on the aircraft, a spectral content of noise in the aircraft, a current fuel consumption rate for the aircraft, or a current fuel load for the aircraft.

Two or more features described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

BRIEF DESCRIPTION OF THE DRAWINGS

FIG. 5 is an example table illustrating application of weights and workload values for data metrics as performed by the pilot workload monitoring engine shown in FIG. 2.

Figure 1:
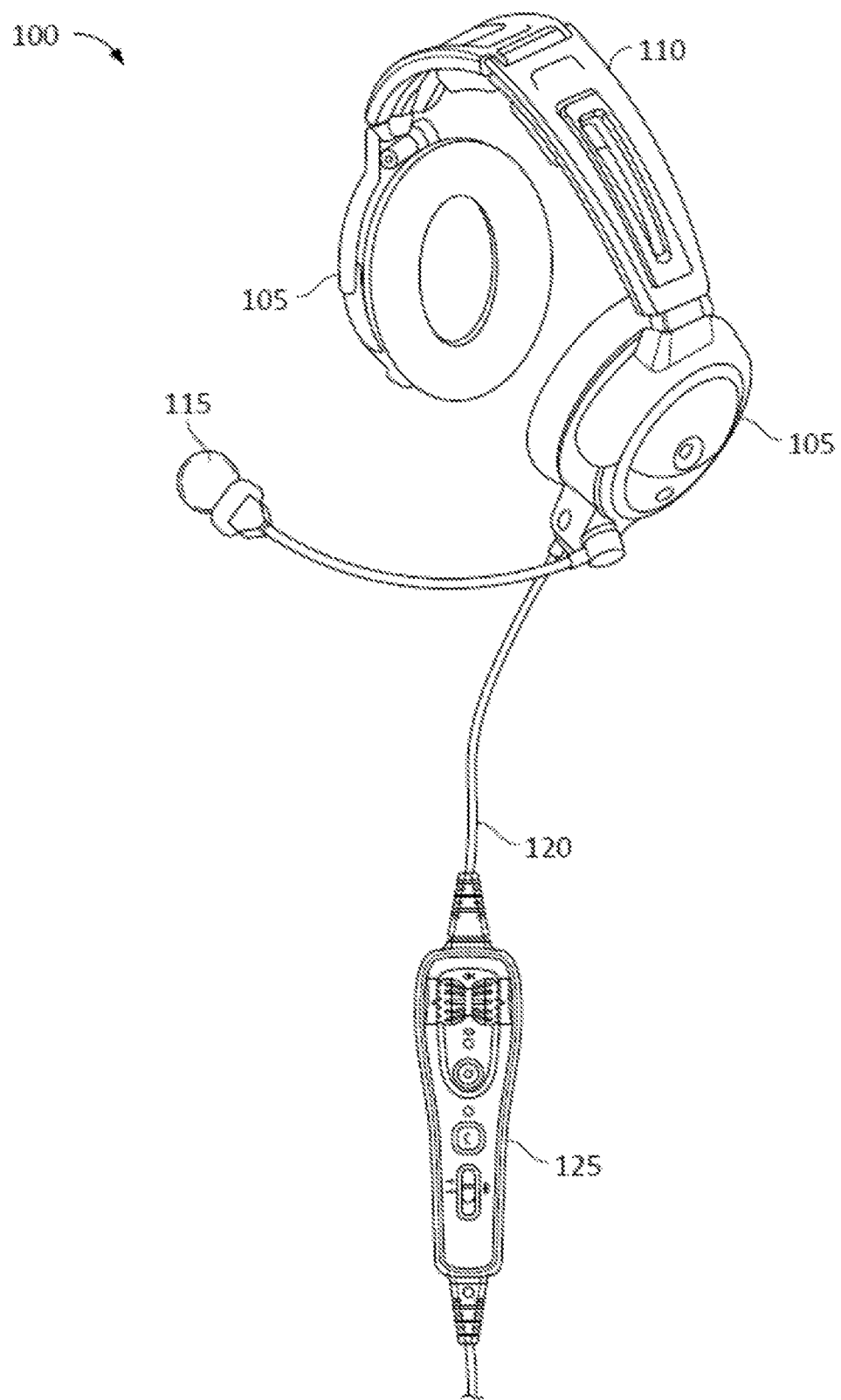
FIG. 1 is a schematic depiction of an aviation headset according to various disclosed implementations.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

This disclosure is based, at least in part, on the realization that pilot workload can be monitored using a variety of non-physiological criteria to aid in situational awareness, fatigue mitigation and/or navigation. For example, a system can use flight condition data and aircraft configuration data to determine pilot workload, and provide a report for use in evaluating that workload, during the flight and/or post-flight.

Commonly labeled components in the FIGURES are considered to be substantially equivalent components for the purposes of illustration, and redundant discussion of those components is omitted for clarity.

Pilot workload management is a consideration applicable to commercial aviation (e.g., larger aircraft), especially for single pilot operations, for operations within instrument meteorological conditions (IMC), or for operations within complex airspace, such as busier airports in the National Airspace System (e.g., Class B Airspace). Workload management considerations are also applicable to "general aviation" (e.g., smaller aircraft, or "GA"), which often involve single pilot operations without autopilot, and therefore without the protections provided by autopilot automation. Additionally, acquisition cost or certification of autopilot in older aircraft may prevent installing autopilot on selected makes or models of GA airplanes. Workload management is also a significant consideration beyond the aviation industry, such as applications in commercial trucking, maritime tanker, military applications, or other applications.

Conventional approaches to monitoring and managing pilot workload focus on situational awareness as derived from physiological data about the pilot, e.g., obtained from physiological sensors on the pilot's flight equipment. While physiological data about the pilot can be useful in determining workload, the conventional approaches fail to fully account for all factors that affect the pilot's workload. These conventional approaches can fail to identify opportunities for corrective action, and can result in unnecessary incidence of pilot fatigue.

In contrast to conventional approaches, various implementations include systems and related methods for assessing pilot workload based upon flight condition data and aircraft configuration data. The system can include a smart device (e.g., an electronic flight bag, tablet, smartphone, personal computer, etc.) that is coupled with both a headset worn by the pilot and a flight management system. The smart device is configured to analyze flight condition data and aircraft configuration data according to user settings and/or a data model for the pilot in order to assess workload. The smart device is further configured to weight particular flight condition data and/or aircraft configuration data to determine workload components. The system can output a report indicating a workload for the pilot based upon the weighted workload components for one or more aircraft configuration metrics and/or flight condition metrics. The report can include an in-flight indicator of the pilot workload, a predictive indicator of the workload for the aircraft pilot at a future time and/or a post-flight report of the pilot workload.

The systems and methods described herein are directed to improving situational awareness, fatigue mitigation, and navigation. These systems and methods may aid in complying with Federal Aviation Administration (FAA) requirements for flight limitations and rest requirements, as described in 14 C.F.R. § 117.

Aviation headsets are used by pilots in both general aviation and commercial aviation. Such headsets can be connected to aircraft communication systems, for example to communicate with air-traffic control (ATC) or with other pilots. The headsets can also be used as a public addressing system, for example, for the pilots to speak with passengers on board the aircraft. The aircraft communication systems typically include an analog communication system such as an intercom. In some cases, such an intercom system can be configured to communicate over the very-high-frequency (VHF) bands (e.g., 18 MHz to 136.975 MHz) wherein each channel is separated from the adjacent ones by a band of pre-specified width (e.g., 8.33 kHz in Europe, 25 kHz elsewhere). An analog modulation technique such as amplitude modulation (AM) can be used for the communications, and the conversations may be performed in simplex mode. In some cases, for example, for trans-oceanic flights, other frequency bands such as high-frequency (HF) bands can be used for satellite communications. Aviation headsets may be used, for example, by pilots and air-traffic controllers to communicate with one another.

An example of an aviation headset 100 is shown in FIG. 1. The headset 100 includes an ear-cup 105 on each side, which fits on, around, or over the ear of a user. Each of the ear-cups 105 houses acoustic transducers or speakers. The headset 100 also includes an over-the-head bridge 110 for connecting the two ear-cups 105. In some implementations, a microphone 115 (e.g., a boom microphone) may be physically connected to one of the ear-cups 105. The headset 100 can be connected to the aircraft intercom system using the connecting cable 120, which may also include a control module 125 that includes one or more controls for the headset 100. The analog signals to and from the aircraft intercom system are transmitted through the wired connection provided by the connecting cable 120. While the example in FIG. 1 illustrates an aviation headset that includes around-ear ear-cups, aviation headsets having other form-factors, including those having in-ear headphones or on-ear headphones, are also compatible with the technology described herein. In an example involving in-ear headphones, the over-the-head bridge may be omitted, and the boom microphone may be attached to the user via the headset or via a separate structure. Also, the term headset, as used in this document, includes various types of acoustic devices that may be used for aviation purposes, including, for example, earphones and earbuds. Additional headset features are disclosed, for example, in U.S. patent application Ser. No. 15/238,259 ("Communications Using Aviation Headsets," filed Aug. 16, 2016), which is incorporated herein by reference in its entirety.

Figure 2:
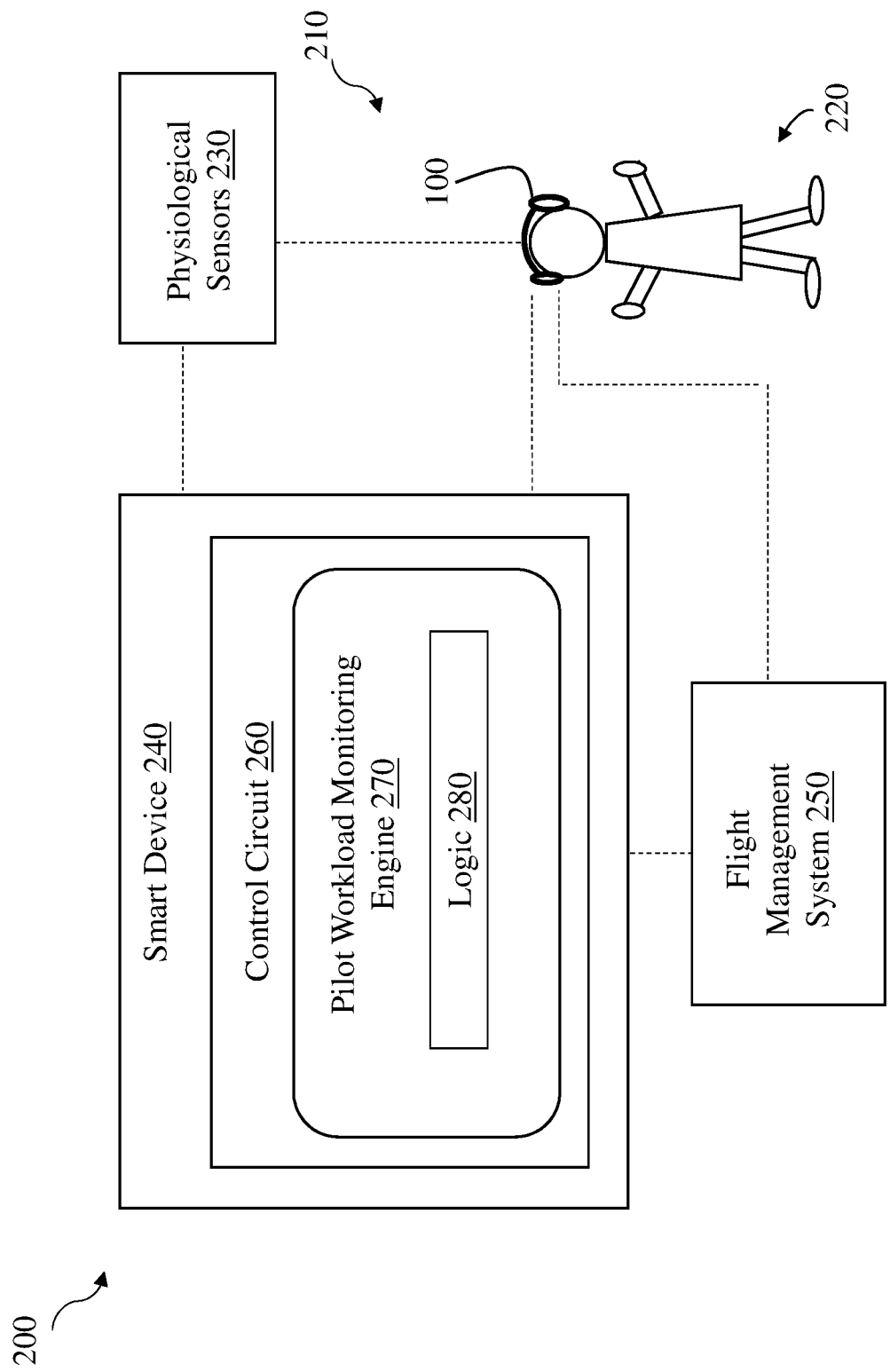
FIG. 2 is a schematic data flow diagram illustrating control processes performed by a pilot workload monitoring engine according to various implementations.

FIG. 2 shows a schematic depiction of data flows in an environment 200 including a pilot monitoring system 210 according to various implementations. In some examples, the environment 200 can include the cabin of an aircraft, however, in various additional implementations, the environment 200 can include the cabin or control room of any piloted vehicle. The pilot monitoring system 210 is shown including the headset 100 as described with reference to FIG. 1, illustrated on a user 220 (e.g., a pilot). The pilot monitoring system 210 can further include one or more physiological sensor(s) 230 for detecting physiological conditions of the pilot 220. The pilot monitoring system 210 can also include a smart device 240 in communication with the headset 100 for performing pilot monitoring functions as described herein. The smart device 240 can be connected with a flight management system 250 that is configured to manage flight conditions according to the prescribed flight pattern.

In various implementations, the physiological sensor(s) 230 are configured to detect physiological conditions about the pilot 220. In some cases, the physiological sensor(s) 230 are located in the headset 100, at the smart device 240 or in another piece of hardware proximate the pilot 220 in the environment 200 (e.g., in a seat, armrest, control apparatus, dashboard, user interface, windshield, etc.). In various implementations, the physiological sensors 230 can include one or more biometric sensors such as a heart rate sensor, a photoplethysmogram (PPG), electroencephalogram (EEG), electrocardiogram (ECG) or EGO) optical/laser-based sensors and/or vision systems for tracking movement or speed, light sensors for detecting time of day, audio sensors (e.g., microphones) for detecting human or other user speech or ambient noise, electrodermal activity (EDA) sensors for detecting electrodermal activity of the pilot, etc. In additional cases, the physiological sensors 230 can include or utilize an inertial measurement unit (IMU) and/or a global positioning system (GPS) to detect pilot movement. In particular cases, the physiological sensors 230 are configured to gather physiological condition data including one or more of: a heart rate of the pilot 220, a heart rate variability of the pilot 220, a blood oxygen saturation level of the pilot 220, an electrical activity from the brain of the pilot 220, an electrical activity from the heart of the pilot 220, a respiration rate of the pilot 220, electrodermal activity of the pilot 220, eye movement of the pilot 220, or body movement and/or position change of the pilot 220.

The flight management system 250 can include at least one computing system (including one or more processors, memory, control circuits, user interface(s), etc.) as well as a communications system (e.g. one or more wireless transceivers, satellite communication/navigation systems, etc.). The flight management system 250 can be configured to maintain communication with one or more air traffic control towers, manage aircraft configuration settings (e.g., autopilot and other in-flight control features), obtain flight condition data from one or more sensors, manage the flight route, and/or manage surrounding aircraft position data (e.g., aircraft traffic data about nearby aircraft).

In some cases, the flight management system 250 receives commands from the pilot 220 to adjust one or more aircraft configuration settings on the aircraft. The pilot 220 can enter and/or adjust aircraft configuration settings using one or more interface commands via a controls interface (e.g., tactile interface, voice interface, gesture interface, etc.). In certain implementations, aircraft configuration settings are adjusted with a control panel positioned proximate the pilot 220. In various implementations, the flight management system 250 is configured to maintain (e.g., receive or otherwise gather) aircraft configuration data, including data about one or more of: power settings of the aircraft, a position of landing gear on the aircraft, a position of wing flaps on the aircraft, a weight of the aircraft, a balance of the aircraft, a number of crew members on the aircraft, a spectral content of noise in the aircraft, a current fuel consumption rate for the aircraft, or a current fuel load for the aircraft.

In some cases, the flight management system 250 is coupled with a network of sensors, both inside the cabin (e.g., in the environment 200) as well as external to the cabin (and in some cases, external to the aircraft). These sensors can include temperature sensors, pressure sensors, humidity sensors, light sensors, wind sensors, etc. The flight management system 250 is configured to maintain (e.g., receive or otherwise gather) flight condition data from the sensors as well as the communications system. In some examples, flight condition data can include data about one or more of: a weather condition proximate the aircraft flown by the pilot 220 during flight, an altitude of the aircraft during flight, a wind condition proximate the aircraft during flight, a deviation of the aircraft from a planned route, surrounding aircraft position data (e.g., including proximity, routes, density, etc.), an amount of turbulence experienced by the aircraft during flight, a total flight time for the aircraft, a distance traveled by the aircraft during flight, or an ambient lighting condition proximate the aircraft during flight.

In various implementations, the smart device 240 is connected with at least one of the headset 100, the physiological sensors 230 or the flight management system 250, and is configured to monitor the workload of the pilot 220 using data from one or more of these connected systems. In various implementations, the smart device 240 is connected with each of the headset 100, the physiological sensors 230 and the flight management system 250.

In some cases, the smart device 240 includes an electronic flight bag. In other cases, the smart device 240 can include one or more personal computing devices (e.g., desktop or laptop computer), wearable smart devices (e.g., smart watch, smart glasses), a smart phone, a tablet, or a remote control device Smart device 240 can include a conventional user interface for permitting interaction with a user, and can include one or more network interfaces for interacting with headset 100, the physiological sensors 230, the flight management system 250 and other components in the environment 200. Smart device 240 can further include embedded sensors for measuring biometric information about user, e.g., body temperature; heart rate; or movement patterns (e.g., via accelerometer(s)). In additional implementations, smart device 240 can access physiological information about the pilot from a locally executed application or an application on another smart device (e.g., the pilot's smart watch, smart phone, exercise watch, etc.). For example, the smart device 240 can access physiological information about the pilot's sleep patterns, duration of sleep, activity level, etc., as tracked by one or more applications running on the smart device 240 or another smart device that is connected with the smart device 240. In various implementations, one or more functions of the flight management system 250 can be executed at smart device 240. Further, it is understood that the flight management system 250 can include any manner of smart device described herein.

The smart device 240 is configured to perform processes to monitor the workload of the pilot 220 according to various implementations. In various implementations, the smart device 240 includes a control circuit 260 for executing functions in pilot workload monitoring as described herein. The control circuit 260 may be implemented as a chipset of chips that include separate and multiple processors, e.g., analog and digital processors. The control circuit 30 may provide, for example, for coordination of other components of the smart device 240, such as control of user interfaces (not shown) and applications run by the smart device 240. The control circuit 260 maintains (e.g., stores) or otherwise accesses and runs (e.g., via a distributed and/or cloud computing platform) a pilot workload management engine 270. The pilot workload management engine 270 can include logic 280 for executing functions described herein. In some cases, the pilot workload management engine 270 includes a software application such as a mobile device application that is configured perform functions in monitoring the workload of pilot 220.

Figure 3:
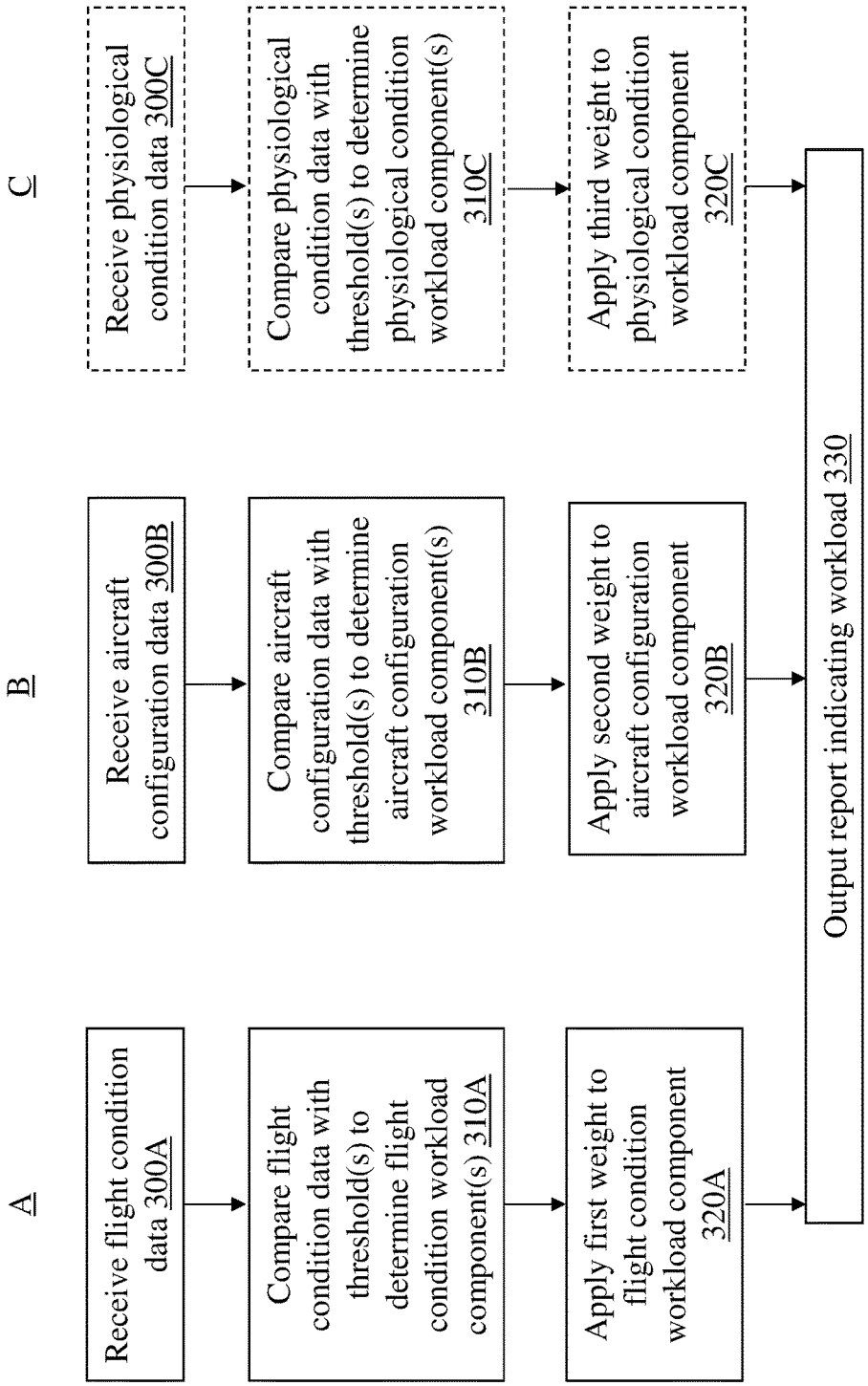
FIG. 3 is a process flow diagram illustrating processes performed by the pilot workload monitoring engine shown in FIG. 2.

FIG. 3 is a flow diagram illustrating processes performed by the pilot workload management engine (or simply, "workload management engine") 270 according to various implementations. With reference to both FIG. 2 and FIG. 3, in various implementations, the workload management engine 270 is configured to receive and analyze data from one or more systems and devices in the environment 200. While distinct lanes (A, B, and C) are shown to illustrate sub-processes performed that can be performed in parallel, it is understood that these processes can also be performed sequentially. As shown in FIG. 3, the workload management engine 270 is configured to receive flight condition data (process 300A) and aircraft configuration data (process 300B) about the aircraft from the flight management system 250. In some additional implementations (shown in phantom as optional), the workload management engine 270 is configured to receive physiological condition data from the physiological sensors 230.

In various implementations, the workload management engine 270 receives the flight condition data and aircraft configuration data on a continuous basis, however, in some cases, this data is received on a periodic basis. Similarly, the workload management engine 270 can receive the physiological condition data from the physiological sensors 230 on a continuous or periodic basis. In some cases, the workload management engine 270 can be configured to receive this flight condition data, aircraft configuration data (and in some cases, physiological condition data) during flight.

The workload management engine 270 is then configured to compare the flight condition data with a flight condition threshold to determine a flight condition workload component (process 310A). Contemporaneously, or sequentially with process 310A, the workload management engine 270 is also configured to compare the aircraft configuration data with an aircraft configuration threshold to determine an aircraft configuration workload component (process 310B). In some cases, contemporaneously, or sequentially with process(es) 310A and/or 310B, the workload management engine 270 is also configured to compare the physiological condition data with a physiological condition threshold to determine a physiological condition workload component (process 310C).

In some particular implementations, the thresholds are based upon predefined settings specific to the aircraft pilot. For example, the flight condition threshold and/or the aircraft configuration threshold can be based upon predefined settings that are specific to the pilot of the aircraft. In one example, the pilot 220 can set and/or adjust predefined settings specific to his/her comfort level or preferences with conditions such as adverse or inclement weather, wind, turbulence, etc. Less experienced pilots may have a greater level of discomfort with such non-ideal conditions, and can enter or adjust pilot-specific settings in the workload management engine 270 to reflect this level of comfort. In a more particular example, the pilot 220 may have a particularly high level of discomfort with flying in weather conditions that include lighting, and can define settings to reflect this level of discomfort. In this case, the workload management engine 270 sets the flight condition data threshold to correspond with the pilot's level of discomfort as reflected by the pilot-adjusted settings. A high level of discomfort with lightning can be reflected in a low lighting threshold for the flight condition data. In another example, a pilot can indicate a comfort level with flying after getting a certain number of hours of sleep (or a certain quality of sleep). In these cases, the plot can define settings to reflect a level of discomfort with flying after one or more nights of X number of hours of sleep or less, or after one or more nights of low quality sleep.

The pilot 220 can define and/or adjust these settings and associated thresholds via a user interface, for example, through an interface connected with the workload management engine 270, e.g., running on the smart device 240 (FIG. 2). In particular implementations, the pilot 220 can insert or adjust values for settings using the interface, e.g., by typing, speaking, selecting or otherwise entering a value within a range for a setting, or gesturing, sliding, or dialing between values for a setting. For example, the pilot 220 can enter a value between X and Y for comfort level with flying in lightning, or can choose a value in the range between X and Y. The pilot 220 can also enter or adjust values for additional conditions such as wind, turbulence, etc.

Figure 4:
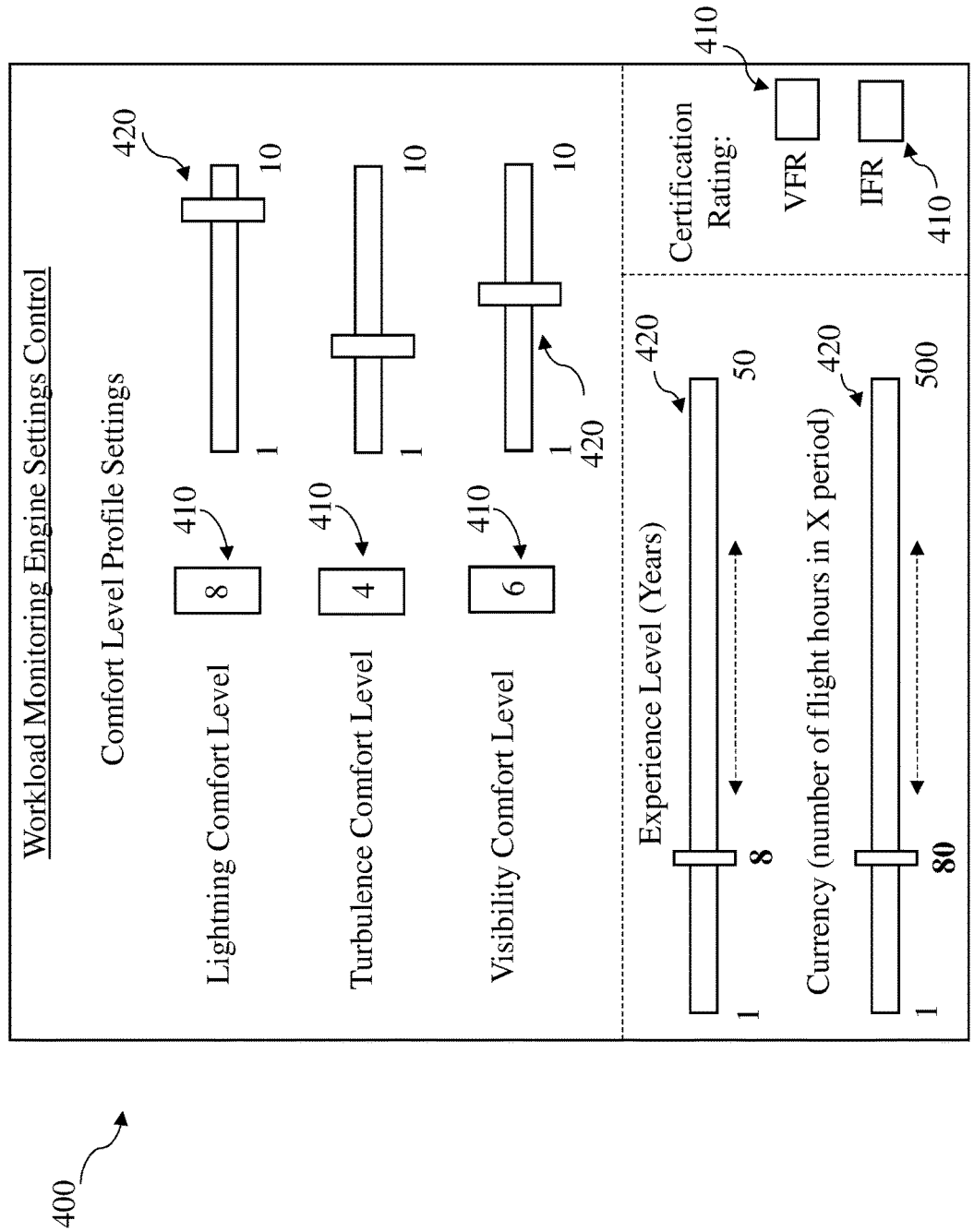
FIG. 4 is an example depiction of a user interface according to various implementations.

An example user interface 400 is illustrated schematically in FIG. 4, which shows settings that can be adjusted by the pilot 220 (FIG. 2) according to various implementations. In certain cases, these settings can be saved in a profile associated with each pilot 220 (FIG. 2), e.g., in the pilot workload monitoring engine 270 or in another accessible system. In this example, Comfort Level inputs are shown as one example, e.g., Lighting Comfort Level, Turbulence Comfort Level and Visibility (e.g., rain/fog) Comfort Level are shown, providing the pilot 220 with the ability to either enter a value (e.g., personal minimum) within a range (e.g., 1-10) in a corresponding input section 410, and/or actuate a slider 420 to adjust the settings value for each parameter. It is understood that the input section 410 and slider 420 may be redundant, and as such, only one of these settings adjustment mechanisms is presented for each setting in some implementations. In this example depiction, another set of profile inputs are shown toward the bottom of the interface 400, including a slider 420 that allows the pilot 220 to enter information about the level of experience that he/she has (e.g., the number of years that the pilot 220 has been flying). Also shown in this section of the interface 400 is a slider 420 for indicating flight currency for the pilot (e.g., a number of times flown within a recent period, such as a number of days, weeks or months).

An additional example profile input is shown in the bottom right-hand side of the interface 400, which allows the pilot to enter information about his/her Certification Rating. In this example, the pilot can enter information about whether he/she is certified to fly under visual flight rules (VFR) and/or instrument flight rules (IFR). In some cases, the input for the Certification Rating can allow the pilot to enter a certification value indicating a level of comfort with one or both of VFR and IFR, or, can allow the pilot to indicate that he/she is certified to conduct a flight under VFR and/or IFR. Operating an aircraft under VFR is not always practical when ambient conditions (e.g., visibility conditions) make visual cues difficult to discern. As such, a pilot that is not comfortable with IFR flight parameters may have a particularly high workload value when visibility is compromised.

Because the input value range for certain settings can encompass a broad range, a slider 420 or similar adjustment mechanism (e.g., dial) can be used where sufficient space on the interface 400 is available. However, it is understood that any adjustment made using a slider 420, dial, or other such mechanism can be made via an input section 410 or another user interface input.

While thresholds are described in some cases as being specific values, e.g., a value of X or Y, it is understood that thresholds can also include ranges of values. For example, exceeding a threshold value for an aircraft configuration such as high wing flap position can be undesirable, but so can falling below a threshold value for that same aircraft configuration, such as a low wing flap position. In these scenarios, a threshold can include a threshold range or band of values, such that deviation from that threshold is indicated as undesirable.

In various implementations, the thresholds used to calculate the workload component can be specific to each data metric evaluated for the flight condition, aircraft condition and/or physiological condition. For example, flight condition data for several data metrics can be compared with particular thresholds for those metrics. It is understood that this can result in many (e.g., dozens) of workload components for the various data metrics considered by the workload management engine 270.

In some cases, the pilot or another user can enter the predefined settings into the workload management engine 270, e.g., as preferences or values within predefined ranges. In additional implementations, the thresholds are based upon a data model defining a physiological fatigue threshold specific to the pilot of the aircraft. In some cases, the data model is developed via simulations with the pilot, simulations with one or more other pilots, and/or with empirical data gathered from one or more pilots operating in the field. In particular cases, the workload management engine 270 can use statistical averages, deviations, etc. from a data set obtained from a plurality of pilots and associated flights in order to construct the thresholds. The thresholds are correlated with physiological fatigue thresholds for the pilot (or a representative pilot), such that values that meet or deviate from the thresholds (e.g., fall below a lower value or exceed an upper value) can indicate danger of physiological fatigue. For example, an EEG reading detected by the physiological sensors 230 (FIG. 1) that is below a threshold value or range can indicate pilot fatigue. In other example, a lack of eye movement (e.g., in terms of frequency and/or range of movement) can indicate pilot fatigue. In still further examples, delayed pilot action (also called "getting behind the aircraft") can indicate pilot fatigue, such as where a pilot is late in making a descent, or reacts to dynamic conditions in a time greater than a desired period (e.g., as derived from an average of a data set, or an industry standard time). In a particular example, a standard descent threshold can be X feet/min (e.g., 1,000 ft/min), and significant deviation from this threshold can be used as a factor to indicate pilot fatigue. In another example, historical data such as GPS/location data from other aircraft making a similar approach can be used to define the data model. In these cases, the pilot workload monitoring engine 270 can use a threshold descent rate that is specific to a particular airport or location in evaluating pilot fatigue.

In example implementations, the data model defining a physiological fatigue threshold for the aircraft pilot includes: a) correlations between flight condition data and physiological fatigue for the aircraft pilot for the plurality of data metrics, b) correlations between aircraft configuration data and physiological fatigue for the aircraft pilot for the plurality of data metrics, and (in some cases), c) correlations between physiological condition data and physiological fatigue for the aircraft pilot for the plurality of data metrics.

In various implementations, the workload component is a value representing the deviation of the received data from the corresponding threshold. In particular examples, a positive value indicates an undesirable deviation, e.g., exceeding a threshold or deviating from a threshold range (either exceeding an upper end or falling below a lower end). In some such cases, a zero or negative value is desirable, e.g., where the value is below (negative) or meets (zero) the threshold. It is understood that this scenario could be reversed, such that a negative value indicates an undesirable deviation, and positive values indicate a desired deviation (e.g., not exceeding a threshold or falling within a desirable threshold range). In any case, the workload component can include a value that represents the deviation in the received data from the corresponding threshold (or threshold range).

As shown in FIG. 3, the workload management engine 270 is also configured to apply a first weight to the flight condition workload component (process 320A) and (either contemporaneously or sequentially) apply a second weight to the aircraft configuration workload component (process 320B) to generate weighted workload components for these factors. In cases where physiological condition data is obtained and compared with a corresponding threshold (processes 300C and 310C, respectively), the workload management engine 270 can also be configured to apply a third weight to the physiological condition workload component to generate a weighted workload component for this factor (process 320C).

In various cases, the first weight, second weight and/or third weight can each include sub-weights assigned to each of a plurality of data metrics in the workload components and/or condition data. For example, as noted herein, the flight condition threshold and the aircraft configuration threshold (and in some cases, the physiological condition threshold) can each include a plurality of (sub) thresholds corresponding with each of the plurality of data metrics. In these cases, one or more distinct sub-weights can be applied to each of the data metric values and/or sub-thresholds. In particular examples, these sub-weights can be assigned or adjusted based upon weight ratios described herein, e.g., based upon the data model defining the physiological fatigue threshold for the pilot 220. In still other examples, the pilot 220 can assign sub-weights to data metrics such as those illustrated in the user interface 400 in FIG. 4. In these cases, with the example of Lightning Comfort Level, Turbulence Comfort Level and Rain/Fog comfort level, the pilot 220 can enter a value in the input 410, and use the slider 420 to apply a weight to that value, e.g., along a scale of the same or different values. In these examples, the workload monitoring engine 270 can use these sub-weight inputs to adjust the overall weight applied to each of the flight conditions, aircraft configuration and/or physiological conditions.

In certain cases, the first weight, second weight and/or third weight is adjusted based upon a number of the data metrics that exceed the corresponding thresholds. For example, in response to detecting that the flight conditions have five (5) data metrics that deviate from their corresponding thresholds, the aircraft configurations have three (3) data metrics that deviate from their corresponding thresholds, and the physiological conditions have one (1) data metric that deviates from its corresponding threshold, the pilot workload management engine 270 can be configured to apply a higher weight to the flight condition workload components than the aircraft configuration workload components, which can have a higher weight than the physiological condition workload components. In some cases, the higher relative weights can be applied to only those metrics that deviate from the threshold. However, in other cases, the higher relative weights can be applied to all metrics within a given workload component type (e.g., flight condition workload components).

In still other cases, the workload management engine 270 assigns higher weights (or sub-weights) to data metrics (e.g., in one or more workload component groups or the physiological condition group) that deviate more significantly from their corresponding threshold. In these cases, where a data metric (e.g., turbulence, wing flap position, or eye movement) deviates from a corresponding threshold by a higher value or percentage than another data metric in that workload component group or physiological condition group, that data metric is assigned a higher weight than the other data metric(s) in that group. In this sense, certain data metrics within a workload component group or the physiological condition group can contribute more significantly (in terms of sub-weight value) to the overall weight (e.g., first weight, second weight, third weight) assigned to that category.

As described herein, the ratio of the weights applied to the flight condition workload component, the aircraft configuration workload component and (if applicable), the physiological condition workload component can be variable based upon one or more factors. That is, these weight ratios can be variable based upon: a) a level of control the pilot can exert over the aircraft condition, b) a value of the flight condition workload component, c) a value of the aircraft configuration workload component, and/or d) a value of the physiological condition workload component.

In some cases, the level of control that the pilot can exert over the aircraft condition is pre-categorized, and can result in distinct (potentially greater) weighting for aircraft configuration data as compared with flight condition data. In these examples, the pilot can take steps to actively control aircraft configuration settings such as landing gear position, wing flap position, fuel consumption rate, etc., whereas flight conditions (e.g., weather conditions, ambient lighting conditions, amount of turbulence) may be impossible or impracticable to control. In one example, aircraft configuration workload components that are more effectively controlled by pilot action can be assigned a distinct weight than those workload components (e.g., other aircraft configuration workload components, flight condition workload components and/or physiological condition workload components) over which the pilot has little or no control. In particular cases, where other values remain equal, aircraft configuration workload components can be assigned a greater weight than the flight condition workload components. For example, as noted herein, controllable physiological factors may be assigned a greater weight in a report that attempts to provide recommended corrective action for the pilot. These controllable physiological factors can include sleep (e.g., duration, quality, number of consecutive nights of X hours), carbon monoxide level, oxygen level, etc. In various implementations, these physiological factors (and/or other factors described herein) can be assigned a highest (maximum) weight when exceeding a corresponding threshold, or subsequent threshold. For example, a slightly low oxygen level can be assigned a medium-to-high weighting, but a severely low oxygen level can be assigned a high-to-maximum weighting in order to indicate the significance of corrective action.

In additional cases, the value of the workload component can dictate the weighting assigned to that component, such as where a higher (or lower) value is assigned a greater weighting. In various implementations, the higher the value of the workload component (indicating undesirable deviation from the threshold or threshold range), the greater the weight that is applied to that workload component. This can enhance the significance of conditions that deviate from the threshold (range).

FIG. 5 shows an example table 500 illustrating workload component values (WCV) and corresponding applied weights for an example set of data metrics. These data metrics can represent various data received from components in the system 200 (FIG. 2), including: a first flight condition (FC(i)), a second flight condition (FC(ii)), a first aircraft configuration (AC(i)), a second aircraft configuration (AC(ii)), a first physiological condition (PC(i)) and a second physiological condition (PC(ii)). As noted herein, workload component values (WCV) indicate a deviation from a threshold (e.g., a value or a range). For the purposes of this example, positive workload component values (WCV) indicate less desirable conditions, such as deviations from the threshold. In the example of table 500, it is evident that the first aircraft configuration (AC(i)) metric has the greatest undesired deviation from the threshold, and also has a high control value, that is, a level of control that the pilot 220 (FIG. 2) can exert over the metric (e.g., on a scale of 0 to 1). In this example, first aircraft configuration (AC(i)) metric could include the position of the wing flaps, or the temperature within the cockpit. These metrics are considered substantially controllable by the pilot 220, e.g., with values above 0.5. In contrast, the first flight condition (FC(i)) metric is shown having a significant undesired deviation from the threshold (e.g., with a value above 2 or 3), but is not controllable by the pilot 220. In this example, the first flight condition (FC(i)) metric could be the ambient weather conditions or the ambient light conditions. Weights can be applied based upon control value, as well as workload component value. Additionally, as noted herein, weights can be applied based upon the category of the metric, for example, flight condition (FC) versus aircraft configuration (AC) versus physiological condition (PC). In this example, based upon the control value of the first aircraft configuration (AC(i)) and its workload component value, this metric has the highest weighted WCV. In particular examples, metrics with a higher weighted WCV can be presented to the pilot 220 (e.g., in any report described herein) as an area where corrective action can have the greatest desirable impact, e.g., by reducing the pilot's workload.

In additional cases, the workload management engine 270 can present metrics to the pilot 220 based upon the pilot's identified level of comfort with one or more of those metrics. For example, where the workload management engine 270 presents a plurality of metrics with a higher weighted WCV to the pilot 220, those metrics identified by the pilot 220 as having a lower relative comfort level (e.g., via an interface such as user interface 400, FIG. 4) can be presented below those metrics that the pilot 220 has either identified as having a higher comfort level or has not identified in terms of comfort level. In these implementations, the workload management engine 270 prioritizes corrective action in metrics for which the pilot 220 has not already identified as being uncomfortable, which may increase the likelihood that the pilot 220 is able to take significant corrective action.

Returning to FIG. 3, after generating the weighted workload components, the workload management engine 270 is configured to compile these weighted workload components (including the weighted flight condition workload component and the weighted aircraft configuration workload component, and in some cases, the weighted physiological condition workload component) and output a report indicating a workload for the pilot based upon those weighted workload components (process 330).

In various implementations, the report includes one or more of: an in-flight indicator of the workload for the aircraft pilot during a flight, a predictive indicator of the workload for the aircraft pilot at a future time, or a post-flight report of the workload for the aircraft pilot throughout the flight. In additional implementations, the report includes suggested adjustments to at least one aircraft configuration metric to reduce the workload for the aircraft pilot. For example, an in-flight report can include suggestions (presented in text or audio form) such as: "Consider dimming the cockpit lights to reduce stress on your eyes." An example pre-flight report can include suggestions such as: "Consider alternate flight pattern to reduce time of flight." An example post-flight report can include notes such as: "The turbulence encountered at Location X increased your stress level by 20%; adjusting altitude and/or path prior to Location X would have mitigated this stress."

Figure 6:
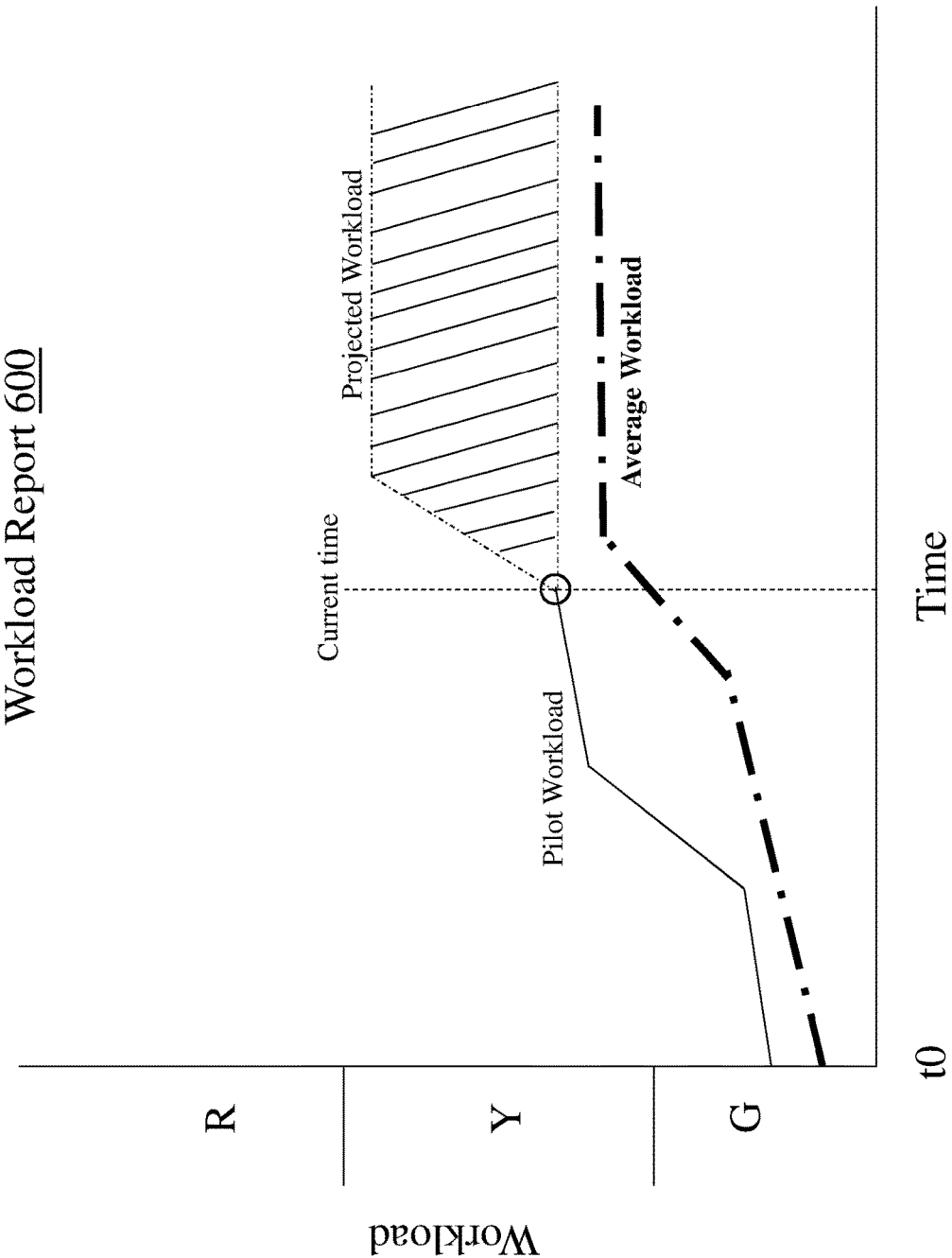
FIG. 6 is an example schematic depiction of a report according to various implementations.

An example workload report 600 is illustrated in graphical form in FIG. 6, indicating workload versus time. The report 600 shows three categories of workload, shown in this black-and-white depiction as G (green), Y (yellow), and R (red). Green indicates an acceptable or target workload, Yellow indicates a workload that is a cause for some concern (e.g., corrective action should be considered), and Red indicates a workload that requires immediate corrective action. The report 600 illustrates past workload for a pilot (left of the "current time" line), as well as the current workload (circled). The report 600 also shows a projected workload for a future time (right of the "current time" line), based upon the pilot's current workload and his/her workload change from t0 to the current time. In certain cases, the projected workload can also be based (in part) upon the data model defining the physiological fatigue thresholds for the pilot(s), e.g., relying upon historical data from the pilot or other pilots to project a future workload, given the pilot's current and past workload, rates of change, and deviations from one or more thresholds. The projected workload is shown in relation to a constant workload at the level shown at the current time.

In certain examples, the report 600 can include a depiction of a statistically average pilot, or target pilot, as compared with the current pilot's workload. In some cases, as noted herein, this "average" pilot can be based upon aggregated data from a plurality of pilots, and can provide the pilot with a time-based comparison of his/her workload to other similarly situated pilots (e.g., based upon similar flight condition data, aircraft configuration data and/or physiological condition data).

The workload management engine 270 shown and described herein can be configured to provide real-time, predictive and post-flight analysis of conditions and configurations that can affect pilot workload and contributed to pilot fatigue. In contrast to conventional approaches that focus on physiological conditions, the approaches described according to various implementations can account for the significant impact that aircraft configuration and flight conditions have on the physiology of the pilot. As such, the workload management engine 270 can provide greater opportunities for corrective and preventative action, as well as analysis, to enhance pilot functions and increase efficiency.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Other embodiments and applications not specifically described herein are also within the scope of the following claims. For example, a headset in accordance with the technology described herein may be configured to receive a phone call while in P2P communication mode. For example, if one of the users communicating over a P2P mode receives a phone call, the corresponding headset can be configured to suspend the P2P communication link temporarily to allow the user to have a private phone call. In such cases, another module (e.g., a Bluetooth® module communicating with a phone) of the headset may be activated upon suspension of the P2P link. In some implementations, the P2P mode may automatically be resumed or reinstated upon termination of the phone call. Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

In various implementations, components described as being "coupled" or "connected" to one another can be joined along one or more interfaces. In some implementations, these interfaces can include junctions between distinct components, and in other cases, these interfaces can include a solidly and/or integrally formed interconnection. That is, in some cases, components that are "coupled" or "connected" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" or "connected" can be linked via conventional hard-wired and/or wireless means such that these electronic components can communicate data with one another. Additionally, sub-components within a given component can be considered to be linked via conventional pathways, which may not necessarily be illustrated.

A number of implementations have been described. Nevertheless, it will be understood that additional modifications may be made without departing from the scope of the inventive concepts described herein, and, accordingly, other embodiments are within the scope of the following claims.

We claim:

1. A pilot monitoring system comprising:
    a headset;
    one or more physiological sensors for detecting physiological conditions of an aircraft pilot; and
    a smart device in communication with the headset and a flight management system, wherein the smart device is configured to:
        receive flight condition data and aircraft configuration data about the aircraft from the flight management system,
        wherein the flight condition data comprises data about at least one of: a weather condition proximate an aircraft flown by the pilot during flight, an altitude of the aircraft during flight, a wind condition proximate the aircraft during flight, a deviation of the aircraft from a planned route, an amount of turbulence experienced by the aircraft during flight, a total flight time for the aircraft, a distance traveled by the aircraft during flight, or an ambient lighting condition proximate the aircraft during flight, and
        wherein the aircraft configuration data comprises data about at least one of: power settings of the aircraft, a position of landing gear on the aircraft, a position of wing flaps on the aircraft, a weight of the aircraft, a balance of the aircraft, a number of crew members on the aircraft, a spectral content of noise in the aircraft, a current fuel consumption rate for the aircraft, or a current fuel load for the aircraft;
        compare the flight condition data with a flight condition threshold to determine a flight condition workload component;
        compare the aircraft configuration data with an aircraft configuration threshold to determine an aircraft configuration workload component;
        apply a first weight to the flight condition workload component and a second weight to the aircraft configuration workload component: and
        output a report indicating a workload for the aircraft pilot based upon the weighted flight condition workload component and the weighted aircraft configuration workload component.

2. The system of claim 1, wherein the smart device is further configured to: receive physiological condition data about the aircraft pilot from the one or more physiological sensors: compare the physiological condition data with a physiological condition threshold to determine a physiological condition workload component; and apply a third weight to the physiological condition workload component, wherein the report indicating the pilot workload is further based upon the weighted physiological condition workload component.

3. The system of claim 1, wherein the smart device comprises an electronic flight bag, and wherein the report comprises at least one of: an in-flight indicator of the workload for the aircraft pilot during a flight, a predictive indicator of the workload for the aircraft pilot at a future time, or a post-flight report of the workload for the aircraft pilot throughout the flight.

4. The system of claim 1, wherein the report comprises suggested adjustments to at least one aircraft configuration metric to reduce the workload for the aircraft pilot.

5. The system of claim 1, wherein at least one of the flight condition threshold or the aircraft configuration threshold is based upon predefined settings specific to the aircraft pilot or a data model defining a physiological fatigue threshold specific to the aircraft pilot, wherein the aircraft pilot is a current pilot of the aircraft, and wherein the first weight is distinct from the second weight.

6. The system of claim 1, wherein a ratio of the first weight to the second weight is variable based upon at least one of: a level of control the aircraft pilot can exert over the aircraft condition, a value of the flight condition workload component or a value of the aircraft configuration workload component.

7. The system of claim 1, wherein the flight condition data and the aircraft configuration data each comprise data inputs from a plurality of data metrics, the flight condition threshold and the aircraft configuration threshold each comprise a plurality of thresholds corresponding with each of the plurality of data metrics, and the first weight and the second weight each include sub-weights applied to each of the respective plurality of data metrics.

8. The system of claim 7, wherein the workload for the aircraft pilot is based upon a data model defining a physiological fatigue threshold for the aircraft pilot, wherein the data model comprises:
    correlations between flight condition data and physiological fatigue for the aircraft pilot for the plurality of data metrics; and
    correlations between aircraft configuration data and physiological fatigue for the aircraft pilot for the plurality of data metrics, wherein at least one of the first weight or the second weight is adjusted based upon a number of the data metrics that deviate from the corresponding thresholds.

9. The system of claim 1, wherein the one or more physiological sensors are configured to detect physiological condition data comprising at least one of: a heart rate of the aircraft pilot, a heart rate variability of the aircraft pilot, a blood oxygen saturation level of the aircraft pilot, an electrical activity from the brain of the aircraft pilot, an electrical activity from the heart of the aircraft pilot, a respiration rate of the aircraft pilot, electrodermal activity of the aircraft pilot, or eye movement of the aircraft pilot.

10. A computer-implemented method of monitoring workload for an aircraft pilot during flight of an aircraft, the method comprising:
receiving flight condition data and aircraft configuration data about the aircraft from a flight management system on the aircraft,
wherein the flight condition data comprises data about at least one of: a weather condition proximate an aircraft flown by the pilot during flight, an altitude of the aircraft during flight, a wind condition proximate the aircraft during flight, a deviation of the aircraft from a planned route, an amount of turbulence experienced by the aircraft during flight, a total flight time for the aircraft, a distance traveled by the aircraft during flight, or an ambient lighting condition proximate the aircraft during flight, and
wherein the aircraft configuration data comprises data about at least one of: power settings of the aircraft, a position of landing gear on the aircraft, a position of wing flaps on the aircraft, a weight of the aircraft, a balance of the aircraft, a number of crew members on the aircraft, or spectral content of noise in the aircraft;
comparing the flight condition data with a flight condition threshold to determine a flight condition workload component;
comparing the aircraft configuration data with an aircraft configuration threshold to determine an aircraft configuration workload component;
applying a first weight to the flight condition workload component and a second weight to the aircraft configuration workload component; and
outputting a report indicating a workload for the aircraft pilot based upon the weighted flight condition workload component and the weighted aircraft configuration workload component.

11. The method of claim 10, further comprising:
receiving physiological condition data about the aircraft pilot from one or more physiological sensors monitoring one or more physiological conditions of the aircraft pilot;
comparing the physiological condition data with a physiological condition threshold to determine a physiological condition workload component; and
applying a third weight to the physiological condition workload component,
wherein the report indicating the workload for the aircraft pilot is further based upon the weighted physiological condition workload component.

12. The method of claim 11, wherein the physiological sensors are configured to detect physiological condition data comprising at least one of: a heart rate of the aircraft pilot, a heart rate variability of the aircraft pilot, a blood oxygen saturation level of the aircraft pilot, an electrical activity from the brain of the aircraft pilot, an electrical activity from the heart of the aircraft pilot, a respiration rate of the aircraft pilot, electrodermal activity of the aircraft pilot, or eye movement of the aircraft pilot.

13. The method of claim 10, wherein the smart device comprises an electronic flight bag, and wherein the report comprises at least one of: an in-flight indicator of the workload for the aircraft pilot during a flight, a predictive indicator of the workload for the aircraft pilot at a future time, or a post-flight report of the workload for the aircraft pilot throughout the flight.

14. The method of claim 10, wherein the report comprises suggested adjustments to at least one aircraft configuration metric to reduce the workload for the aircraft pilot.

15. The method of claim 10, wherein at least one of the flight condition threshold or the aircraft configuration threshold is based upon predefined settings specific to the aircraft pilot or a data model defining a physiological fatigue threshold specific to the aircraft pilot, wherein the aircraft pilot is a current pilot of the aircraft, and wherein the first weight is distinct from the second weight.

16. The method of claim 10, wherein a ratio of the first weight to the second weight is variable based upon at least one of: a level of control the aircraft pilot can exert over the aircraft condition, a value of the flight condition workload component or a value of the aircraft configuration workload component.

17. The method of claim 10, wherein the flight condition data and the aircraft configuration data each comprise data inputs from a plurality of data metrics, the flight condition threshold and the aircraft configuration threshold each comprise a plurality of thresholds corresponding with each of the plurality of data metrics, and the first weight and the second weight each include sub-weights applied to each of the respective plurality of data metrics.

18. The method of claim 17, wherein the workload for the aircraft pilot is based upon a data model defining a physiological fatigue threshold for the aircraft pilot, wherein the data model comprises:
correlations between flight condition data and physiological fatigue for the aircraft pilot for the plurality of data metrics; and
correlations between aircraft configuration data and physiological fatigue for the aircraft pilot for the plurality of data metrics,
wherein at least one of the first weight or the second weight is adjusted based upon a number of the data metrics that deviate from the corresponding thresholds.

19. A computer-implemented method of monitoring workload for an aircraft pilot during flight of an aircraft, the method comprising:
receiving flight condition data and aircraft configuration data about the aircraft from a flight management system on the aircraft;
comparing the flight condition data with a flight condition threshold to determine a flight condition workload component;
comparing the aircraft configuration data with an aircraft configuration threshold to determine an aircraft configuration workload component;
applying a first weight to the flight condition workload component and a second weight to the aircraft configuration workload component,
wherein a ratio of the first weight to the second weight is variable based upon at least one of: a level of control the aircraft pilot can exert over the aircraft condition, a value of the flight condition workload component or a value of the aircraft configuration workload component; and outputting a report indicating a workload for the aircraft pilot based upon the weighted flight condition workload component and the weighted aircraft configuration workload component.

20. The method of claim 19, wherein the report comprises suggested adjustments to at least one aircraft configuration metric to reduce the workload for the aircraft pilot.

* * * * *